(12) United States Patent
Ohhashi et al.

(10) Patent No.: US 7,344,504 B2
(45) Date of Patent: Mar. 18, 2008

(54) VENOUS DISTENSIBILITY EVALUATION INDEX MEASURING APPARATUS

(75) Inventors: Toshio Ohhashi, Matsumoto (JP); Hideki Hosoi, Akita (JP)

(73) Assignee: Tanita Corporation, Tokyo (JP)

(*) Notice: Subject to any disclaimer, the term of this patent is extended or adjusted under 35 U.S.C. 154(b) by 878 days.

(21) Appl. No.: 10/755,228

(22) Filed: Jan. 13, 2004

(65) Prior Publication Data
US 2004/0167412 A1   Aug. 26, 2004

(30) Foreign Application Priority Data
Feb. 25, 2003   (JP) .............................. 2003-046795

(51) Int. Cl.
*A61B 5/02*   (2006.01)
*A61B 5/04*   (2006.01)

(52) U.S. Cl. ...................... 600/506; 600/481; 600/547; 600/483; 600/504

(58) Field of Classification Search ................ 600/481, 600/483–485, 490–506, 507, 547
See application file for complete search history.

(56) References Cited

U.S. PATENT DOCUMENTS

| | | | |
|---|---|---|---|
| 3,996,924 A | | 12/1976 | Wheeler |
| 3,996,925 A | * | 12/1976 | Djordjevich ................ 600/506 |
| 4,144,878 A | * | 3/1979 | Wheeler ...................... 600/506 |
| 4,204,545 A | * | 5/1980 | Yamakoshi ................. 600/506 |
| 4,314,563 A | * | 2/1982 | Wheeler ...................... 600/506 |
| 4,437,469 A | * | 3/1984 | Djordjevich et al. ........ 600/485 |
| 4,548,211 A | * | 10/1985 | Marks ......................... 600/507 |
| 4,562,843 A | * | 1/1986 | Djordjevich et al. ........ 600/485 |
| 4,660,566 A | * | 4/1987 | Palti ............................ 600/490 |
| 4,873,987 A | | 10/1989 | Djordjevich et al. |

(Continued)

FOREIGN PATENT DOCUMENTS

EP    1452131 A1 *  9/2004

(Continued)

OTHER PUBLICATIONS

"Standard Physiology", 4th edition, Mar. 1, 1999 (3rd impression), pp. 508-509, edited by T. Hongo, T. Hiroshige, J. Toyoda, and M. Kumada.

*Primary Examiner*—Charles A. Marmor, II
*Assistant Examiner*—Navin Natnithithadha
(74) *Attorney, Agent, or Firm*—McDermott Will & Emery LLP

(57) ABSTRACT

In an venous distensibility evaluation index measuring apparatus, a pressure adjusting section generates a pressure to supply it to a venous occluding section; in response thereto the venous occluding section starts to press a vein in the upper arm; upon this operation, an electrode section causes a current to flow, while detecting a voltage at that time; an impedance conversion section converts this detected voltage in combination with the supplied current into an impedance; an impedance transition gradient calculating unit determines a gradient of a rate of change in impedance to the elapsed time; a venous distensibility evaluation index determining unit determines a venous age corresponding to said gradient of the rate of change in impedance to the elapsed time as well as a venous sclerosis level corresponding to the venous age based on the relation data stored previously in a storage section; and finally a display section indicates the venous age and the venous sclerosis level.

26 Claims, 6 Drawing Sheets

U.S. PATENT DOCUMENTS 5,090,417 A * 2/1992 Mollan et al. ............... 600/504
5,241,963 A * 9/1993 Shankar ...................... 600/481
5,297,556 A * 3/1994 Shankar ...................... 600/481
5,343,867 A * 9/1994 Shankar ...................... 600/481
7,118,534 B2 * 10/2006 Ward et al. ................. 600/490

FOREIGN PATENT DOCUMENTS

FR             2703900         10/1994

\* cited by examiner

| VENOUS AGE | VENOUS SCLEROSIS LEVEL | POSSIBILITY OF VASCULAR DISEASE |
|---|---|---|
| ~39(YEARS) | LEVEL 0 | EXTREMELY LOW |
| 40~49(YEARS) | LEVEL 1 | LOW |
| 50~59(YEARS) | LEVEL 2 | A LITTLE HIGHER |
| 65(YEARS)~ | LEVEL 3 | HIGH |

EVALUATION RESULT FOR YOUR VENOUS DISTENSIBILITY

| | |
|---|---|
| ACTUAL AGE : | 34 YEARS |
| VENOUS AGE : | 26 YEARS |
| VENOUS SCLEROSIS LEVEL : | LEVEL 0 |

ADVICE :

THE POSSIBILITY OF THE VASCULAR DISEASE IS EXTREMELY LOW.
CONTINUE YOUR CURRENT LIVING HABIT CAUTIOUSLY WITH REGULAR CHECK-UP TO BE HEALTHY.

VENOUS DISTENSIBILITY EVALUATION INDEX MEASURING APPARATUS

BACKGROUND OF THE INVENTION

1. Field of the Invention

The present invention relates to a venous distensibility evaluation index measuring apparatus that provides a measurement on an evaluation index for a venous distensibility.

2. Description of the Prior Art

As for the evaluation of the venous distensibility according to the prior art, there has been employed a venous occlusion plethysmography (see the nonpatent reference 1, for example) by way of the impedance method, in which forearm veins are compressed by a cuff to thereby cause the blood to be stored in a terminal region of a body distant from the heart (i.e., in the hand side), and a change in volume of veins is measured, wherein the evaluation has been given based on a variation in the volume of the forearm veins per unit time in such a manner that if a gradient of the variation in the volume of the forearm veins per unit time is large, it is determined that the blood can flow easily, and if the gradient of the variation in the volume thereof per unit time is small, it is determined that the blood is difficult to flow.

Nonpatent Reference 1

"*Standard Physiology*", 4th edition, Mar. 1, 1999 (3rd impression), pp. 508-509, edited by T. Hongo, T. Hiroshige, J. Toyoda, and M. Kumada.

The venous occlusion plethysmography by way of the impedance method described above, however, can simply measure the volumetric change in the veins, but it has inhibited the evaluation of the venous distensibility based on the measured result by this method, unless technicians such as physicians provide instructions thereon.

In this connection, an object of the present invention, in the light of the circumstances described above, is to provide a venous distensibility evaluation index measuring apparatus that can provide an evaluation of the venous distensibility in a simple and convenient manner.

SUMMARY OF THE INVENTION

To accomplish the above-described object, according to an aspect of the present invention, there is provided a venous distensibility evaluation index measuring apparatus comprising: a venous occluding section; a pressure adjusting section; a clock section; an electrode section; an impedance conversion section; an impedance transition gradient calculating unit; a storage section; a venous distensibility evaluation index determining unit; and a display section, whereby said venous occluding section causes a vein in one part of body regions to be in a pressed condition; said pressure adjusting section adjusts a pressure used to cause the vein in the one part of the body regions to be in the pressed condition by increasing or decreasing the pressure, which is to be supplied to said venous occluding section; said clock section measures an elapsed time since said venous occluding section has started the pressing operation of said vein in the one part of the body regions; said electrode section supplies a current at a predetermined frequency to a vein in a location more distant from the heart with respect to that of the venous occluding section yet in the same circulation path as said vein of the one part of the body regions, while detecting a voltage, when said clock section measures said elapsed time; said impedance conversion section generates said current at the predetermined frequency to be supplied by said electrode section, while converting said voltage detected by said electrode section in combination with the supplied current into an impedance; said impedance transition gradient calculating unit arithmetically calculates a gradient of a rate of change in impedance to the elapsed time based on said impedance converted in said impedance conversion section and said elapsed time measured by said clock section; said storage section stores previously data indicative of a relation between the gradient of the rate of change in impedance to the elapsed time and a first venous distensibility evaluation index; said venous distensibility evaluation index determining unit specifies said first venous distensibility evaluation index corresponding to said gradient of the rate of change in impedance to the elapsed time calculated by said impedance transition gradient calculating unit from said relation data stored previously in said storage section; and said display section indicates said first venous distensibility evaluation index specified by said venous distensibility evaluation index determining unit. With this apparatus, it has been made possible, by bringing the vein in one part of the body regions into the pressed condition by using the venous occluding section, that the volumetric change due to an expansion of the vein in a location more distant from the heart with respect to that of the venous occluding section yet in the same circulation path as the vein of the one part of the body regions maybe detected by the electrode section, the detected data may be converted into the impedance by the impedance conversion section, the gradient of the rate of change in impedance to the elapsed time may be determined by the impedance transition gradient calculating unit, the evaluation index of the volumetric change due to the expansion of the vein or the evaluation index of the venous distensibility may be specified by the venous distensibility evaluation index determining unit, and finally thus specified evaluation index of the venous distensibility may be indicated by the display section. Therefore, the evaluation index of the venous distensibility can be determined and informed of in a simple and convenient way without disturbing any intervenient persons.

Further, the apparatus is characterized in that said pressed condition represents a condition pressed at a constant pressure in a range from 30 mmHg to 90 mmHg. With this apparatus, the vein in one part of the body regions can be occluded exclusively.

Yet further, the apparatus is characterized in that said pressed condition represents a condition pressed at a constant pressure of 50 mmHg. With this apparatus, the vein in one part of the body regions can be exclusively and reliably occluded.

Still further, the apparatus is characterized in that said predetermined frequency is in a range from 1 kHz to 500 kHz. With this apparatus, the volumetric change due to the expansion of the vein can be reliably detected.

Further, the apparatus is characterized in that said predetermined frequency is 4 kHz. With this apparatus, the volumetric change due to the expansion of the vein can be reliably detected.

Yet further, the apparatus is characterized in that said first venous distensibility evaluation index is either one of a venous age or a venous sclerosis level. With this apparatus, the venous age or the venous sclerosis level having an association with a vascular disease can be output. Thus, the evaluation directed to the prediction of the possible vascular disease can be provided.

Still further, the apparatus is characterized in that said storage section stores a correlational expression $Va=-\gamma \times Sit+\delta$ as the relation data between the gradient of the rate of change in impedance to the elapsed time and the venous age, where the Sit denotes the gradient of the rate of change in impedance to the elapsed time, the Va denotes the venous age, and the γ and the δ denote coefficients, respectively, and that said venous distensibility evaluation index determining unit calculates said venous age corresponding to said gradient of the rate of change in impedance to the elapsed time calculated by said impedance transition gradient calculating unit based on said correlational expression stored previously in said storage section. With this apparatus, since the correlational expression Va=−γ×Sit+δ representing the relation that the venous age is getting lower as the gradient of the rate of change in impedance is getting increased is in consistent with a typical tendency of the vein getting hardened in association with the age increase (due to the fact that as the vein gets hardened in association with the age increase, associatively with this hardening, the process of the expansion of the vein becomes slower and thus in association with the slower process of the expansion, the process of the volumetric change in the blood vessel also becomes slower, which in turn slows down the process of the rate of change in impedance featuring this volumetric change), therefore particularly the venous age can be accurately determined.

Further, the apparatus is characterized in that said storage section further stores previously data indicative of a relation between said first venous distensibility evaluation index and a second venous distensibility evaluation index, and that said venous distensibility evaluation index determining unit specifies said second venous distensibility evaluation index corresponding to said first venous distensibility evaluation index specified previously, from said relation data stored further previously in said storage section. With this apparatus, a plurality of evaluation indices involving in the venous distensibility can be output.

Still further, the apparatus is characterized in that said first venous distensibility evaluation index represents either one of the venous age or the venous sclerosis level, and that said second venous distensibility evaluation index represents the venous sclerosis level if said first venous distensibility evaluation index is the venous age, and it represents the venous age if said first venous distensibility evaluation index is the venous sclerosis level. With this apparatus, the venous age and the venous sclerosis level having a relation with the vascular disease can be output. Therefore, the evaluation can be provided from broadly different points of view with respect to the prediction of the possible vascular disease.

Further, the apparatus is characterized in that said storage section stores a correlational expression Va=−γ×Sit+δ as the relation data between the gradient of the rate of change in impedance to the elapsed time and the venous age, where the Sit denotes the gradient of the rate of change in impedance to the elapsed time, the Va denotes the venous age, and the γ and the δ denote coefficients, respectively, and it further stores corresponding data as the relation data between the venous age and the venous sclerosis level, which is indicated by the level 0 of the venous sclerosis level for the venous age no older than 39, the level 1 for the venous age in a range of 40 to 49, the level 2 for the venous age in a range of 50 to 59 and the level 3 for the venous age no younger than 65, and that said venous distensibility evaluation index determining unit specifies said venous age corresponding to said gradient of the rate of change in impedance to the elapsed time calculated by said impedance transition gradient calculating unit based on said correlational expression stored previously in said storage section, and it further specifies said venous sclerosis level corresponding to said venous age calculated previously, from said corresponding data stored further previously in said storage section. With this apparatus, since the correlational expression Va=−γ×Sit+δ representing the relation that the venous age is getting lower as the gradient of the rate of change in impedance is getting increased is in consistent with a typical tendency of the vein getting hardened in association with the age increase (due to the fact that as the vein gets hardened in association with the age increase, associatively with this hardening, the process of the expansion of the vein becomes slower and thus in association with the slower process of the expansion, the process of the volumetric change in the blood vessel also becomes slower, which in turn slows down the process of the rate of change in impedance featuring this volumetric change), therefore particularly the venous age can be accurately determined. Besides, since the venous sclerosis level has a relation with the venous age, an accurate determination on the venous sclerosis level also can be provided.

In accordance with another aspect of the present invention, there is provided a venous distensibility evaluation index measuring apparatus comprising: a venous occluding section; a pressure adjusting section; a clock section; an electrode section; an impedance conversion section; an impedance transition gradient calculating unit; a storage section; a venous distensibility evaluation index determining unit; and a display section, whereby said venous occluding section causes a vein in one part of body regions to be shifted from a pressed condition into a decompressed condition; said pressure adjusting section adjusts a pressure used to cause the vein in the one part of the body regions to be shifted from the pressed condition into the decompressed condition by increasing or decreasing the pressure, which is to be supplied to said venous occluding section; said clock section measures an elapsed time since said venous occluding section has started the decompressing operation of said vein in the one part of the body regions; said electrode section supplies a current at a predetermined frequency to a vein in a location more distant from the heart with respect to that of the venous occluding section yet in the same circulation path as said vein of the one part of the body regions, while detecting a voltage, when said clock section measures said elapsed time; said impedance conversion section generates said current at the predetermined frequency to be supplied by said electrode section, while converting said voltage detected by said electrode section in combination with the supplied current into an impedance; said impedance transition gradient calculating unit arithmetically calculates a gradient of a rate of change in impedance to the elapsed time based on said impedance converted in said impedance conversion section and said elapsed time measured by said clock section; said storage section stores previously data indicative of a relation between the gradient of the rate of change in impedance to the elapsed time and a first venous distensibility evaluation index; said venous distensibility evaluation index determining unit specifies said first venous distensibility evaluation index corresponding to said gradient of the rate of change in impedance to the elapsed time calculated by said impedance transition gradient calculating unit from said relation data stored previously in said storage section; and said display section indicates said first venous distensibility evaluation index specified by said venous distensibility evaluation index determining unit. With this apparatus, it has been made possible, by bringing the vein in one part of the body regions from the pressed condition into the decompressed condition by using the venous occluding section, that the volumetric change due to a contraction (recovery) of the vein in the location more distant from the heart with respect to that of the venous occluding section yet in the same circulation path as the vein of the one part of the body regions may be detected by the electrode section, the detected data may be converted into the impedance by the impedance conversion section, the gradient of the rate of change in impedance to the elapsed time may be determined by the impedance transition gradient calculating unit, the evaluation index of the volumetric change due to the contraction (recovery) of the vein or the evaluation index of the venous distensibility may be specified by the venous distensibility evaluation index determining unit, and finally thus specified evaluation index of the venous distensibility may be indicated by the display section. Therefore, the evaluation index of the venous distensibility can be determined and informed of in a simple and convenient way without disturbing any intervenient persons.

Further, the apparatus is characterized in that said pressed condition represents a condition pressed at a constant pressure in a range from 30 mmHg to 90 mmHg. With this apparatus, the vein in one part of the body regions can be occluded exclusively.

Yet further, the apparatus is characterized in that said pressed condition represents a condition pressed at a constant pressure of 50 mmHg. With this apparatus, the vein in one part of the body regions can be exclusively and reliably occluded.

Still further, the apparatus is characterized in that said predetermined frequency is in a range from 1 kHz to 500 kHz. With this apparatus, the volumetric change due to the contraction (recovery) of the vein can be reliably detected.

Further, the apparatus is characterized in that said predetermined frequency is 4 kHz. With this apparatus, the volumetric change due to the contraction (recovery) of the vein can be more reliably detected.

Still further, the apparatus is characterized in that said first venous distensibility evaluation index is either one of a venous age or a venous sclerosis level. With this apparatus, the venous age or the venous sclerosis level having a relation with the vascular disease can be output. Thus, the evaluation directed to the prediction of the possible vascular disease can be provided.

Yet further, the apparatus is characterized in that said storage section further stores previously data indicative of a relation between said first venous distensibility evaluation index and a second venous distensibility evaluation index, and that said venous distensibility evaluation index determining unit specifies said second venous distensibility evaluation index corresponding to said first venous distensibility evaluation index specified previously, from said relation data stored further previously in said storage section. With this apparatus, a plurality of evaluation indices involving in the venous distensibility can be output.

Yet further, the apparatus is characterized in that said first venous distensibility evaluation index represents either one of the venous age or the venous sclerosis level, and that said second venous distensibility evaluation index represents the venous sclerosis level if said first venous distensibility evaluation index is the venous age, and it represents the venous age if said first venous distensibility evaluation index is the venous sclerosis level. With this apparatus, the venous age and the venous sclerosis level having a relation with the vascular disease can be output. Therefore, the evaluation can be provided from broadly different points of view with respect to the prediction of the possible vascular disease.

BRIEF DESCRIPTION OF THE DRAWINGS

FIG. 7 shows a display section illustrating an exemplary indication of an evaluation result of a venous distensibility.

DESCRIPTION OF THE PREFERRED EMBODIMENT

Preferred embodiments of the present invention will now be described with reference to the attached drawings.

Figure 1:
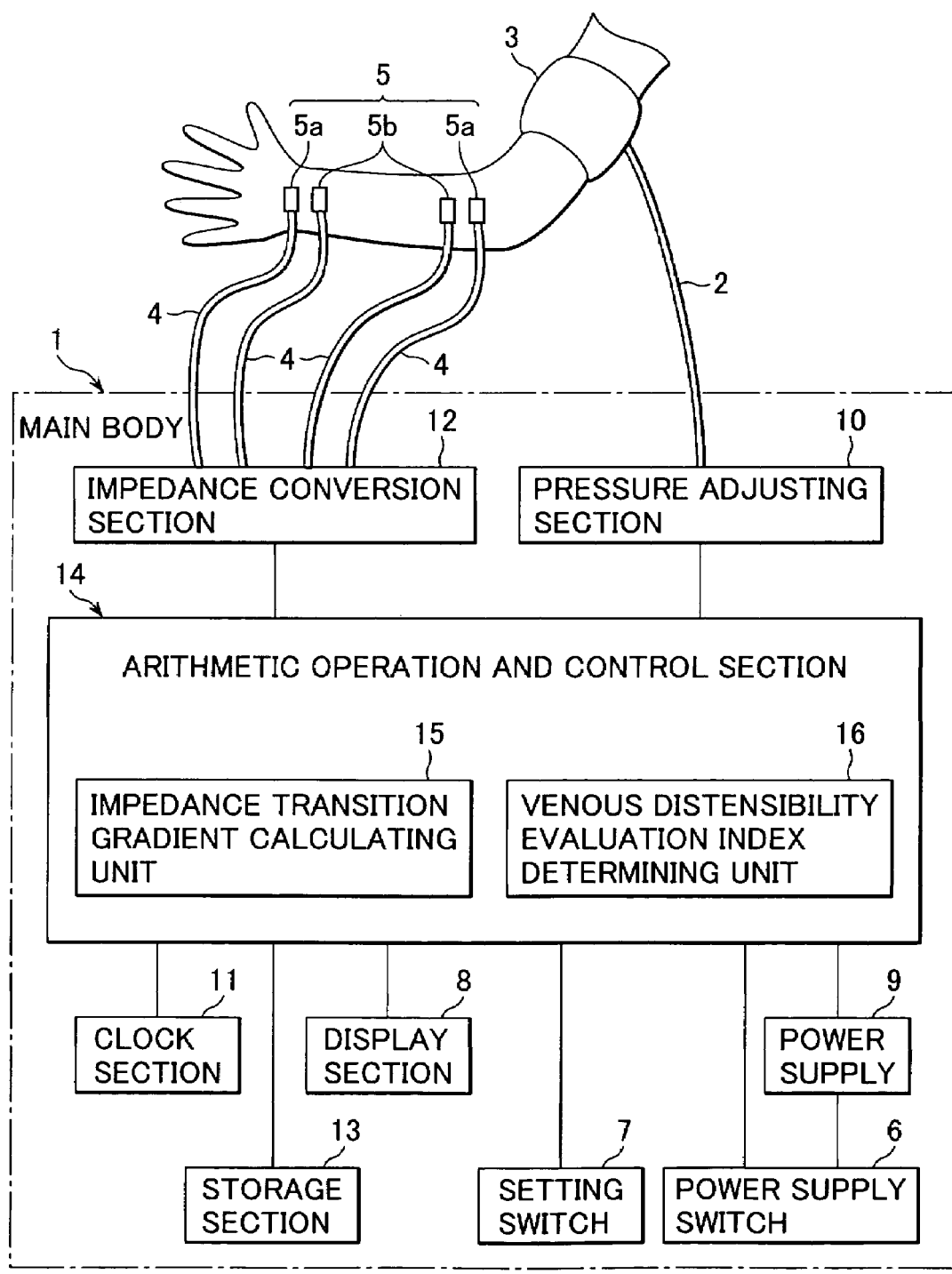
FIG. 1 is a block diagram showing a configuration of a venous distensibility evaluation index measuring apparatus according to the present invention.

First of all, a configuration of a venous distensibility evaluation index measuring apparatus according to the present invention will be described with reference to a block diagram of FIG. 1.

A venous distensibility evaluation index measuring apparatus according to the present invention comprises a main body 1, a venous occluding section 3 connected with the main body 1 by an air tube 2 and an electrode section 5 connected with the main body 1 by a cord 4.

The venous occluding section 3 causes a vein in one part of body regions to be in a pressed condition or to be shifted from the pressed condition into a decompressed condition. To describe this more specifically, the venous occluding section 3 is represented by a manchette (a cuff band), which is typically included in a known hemodynamometer and is used by wrapping and tightening around an upper arm region.

The electrode section 5 supplies a current at a predetermined frequency to a vein in a location more distant from the heart with respect to that of the venous occluding section 3 yet in the same circulation path as the vein in the one part of the body regions, while detecting a voltage. To describe in more specific, the electrode section 5 comprises such electrodes (conducting electrodes 5a, measuring electrodes 5b) to be affixed on the body regions as employed typically in a well-known bioelectric impedance measuring apparatus, in which said conducting electrodes 5a are affixed to the forearm at a certain space so as to supply a current mainly to the vein, and said measuring electrodes 5b are affixed to the forearm at locations on a current flow path so as to thus detect a voltage between the points on the current flow paths of the forearm.

The main body 1 comprises a power supply switch 6, a setting switch 7 and a display section 8, all of which are located in an exterior of the main body 1, and a power supply 9, a pressure adjusting section 10, a clock 11, an impedance conversion section 12, a storage section 13 and an arithmetic operation and control section 14, all of which are located in an interior of the main body 1.

The power supply switch 6 controls a switching between a supply and a stop of an electric power to respective elements of an electric system. The power supply 9 supplied the electric power to the respective elements of the electric system when the power supply switch 6 is shifted to ON state. The setting switch 7 is used to input and then set and register an age and other physical information. The display section 8 serves to indicate a venous age as a first index for evaluating a venous distensibility (a first venous distensibility evaluation index) and a venous sclerosis level as a second index for evaluating the venous distensibility (a second venous distensibility evaluation index). It is to be noted that the term of "venous distensibility" in the present specification refers to a nature of the vein that is expanded to be elongated and extended and is contracted (recovered) from the expanded state back to the original state.

The pressure adjusting section 10 adjusts a pressure to be supplied to the venous occluding section 3 by increasing or decreasing it, which is used to cause a vein in one part of body regions exclusively to be in a pressed condition and/or to be shifted from the pressed condition into a decompressed condition. To describe in more specific, the pressure adjusting section 10 are composed of a pressure sensor, a pressurizing device, an exhaust valve and the like, which are typically employed in a well-known hemodynamometer, and functions in response to the control from the arithmetic operation and control section 14 to increase the pressure up to 50 mmHg in about three seconds and/or to decrease the pressure from this pressurized condition down to 0 mmHg in about two seconds and to maintain this pressure condition.

The clock section 11 measures an elapsed time since the venous occluding section 3 has started the pressing or decompressing operation of the vein in the one part of the body regions. To describe in more specific, the clock section 11 measures the elapsed time for 30 seconds after the starting of the pressing operation on the vein in the one part of the body regions and also for 30 seconds after the starting of the decompressing operation of the pressed condition on the vein in the one part of the body regions.

The impedance conversion section 12 generates the current at a predetermined frequency which is to be supplied through the conducting electrodes 5a, and also converts the voltage detected by the measuring electrodes 5b in combination with the applied current into the impedance. To describe in more specific, the impedance conversion section 12 is composed of a constant voltage generating circuit, a voltage-current converting circuit, am amplifying circuit, an A/D converting circuit, an impedance arithmetic operation section and so on, all of which are typically employed in a well-known bioelectric impedance measuring apparatus, and it applies the current with a frequency of 4 kHz between the electrodes and calculates an impedance based on the detected voltage and the applied current as well-known in the art.

Figures 5, 6:
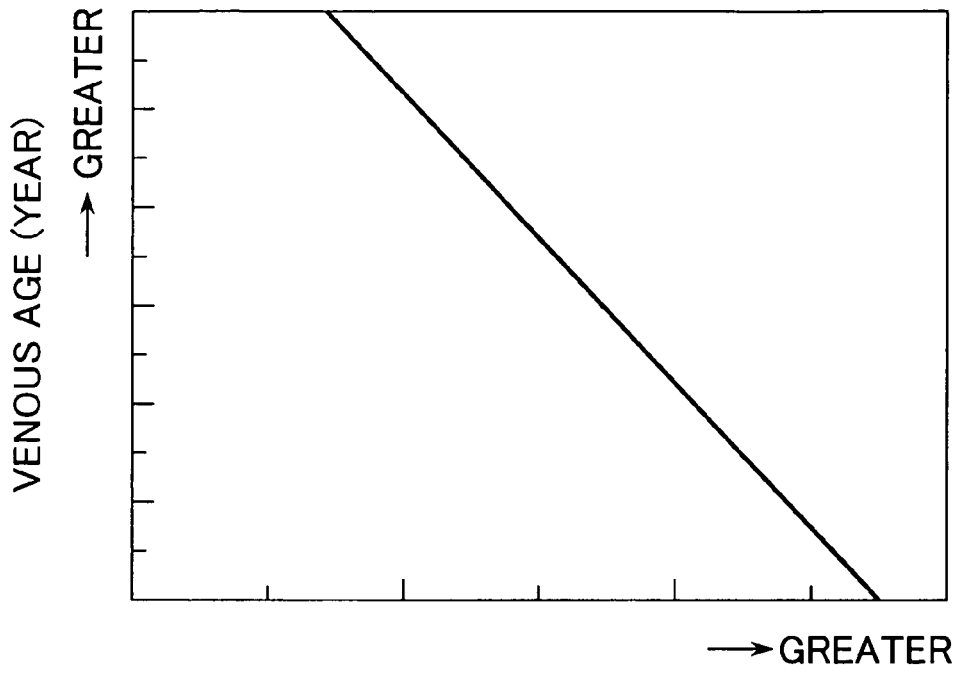
FIG. 5 is a graphical representation showing a relation between a venous age and a gradient of a rate of change in impedance to an elapsed time.
FIG. 6 is a table showing a relation between a venous age and a venous sclerosis level.

The storage section 13 stores in advance data indicative of a relation between a venous age and a gradient of a rate of change in impedance to the elapsed time as well as data indicative of a relation between the venous age and the venous sclerosis level, and also stores data in such respective processes as well-known in the art. To describe in more specific, the storage section 13 stores a correlational expression, $Va = -\gamma \times Sit + \delta$, as the relation data between the venous age and the gradient of the rate of change in impedance to the elapsed time, as shown in the graphical representation of FIG. 5, where the Sit denotes the gradient of the rate of change in impedance to the elapsed time, the Va denotes the venous age, and the $\gamma$ and the $\delta$ denote coefficients, respectively, and it further stores corresponding data as the relation data between the venous age and the venous sclerosis level as shown in the table of FIG. 6, which is indicated by the level 0 of the venous sclerosis level for the venous age no older than 39, the level 1 for the venous age in a range of 40 to 49, the level 2 for the venous age in a range of 50 to 59 and the level 3 for the venous age no younger than 65. In addition, the storage section 13 further stores the age and other physical information to be entered through the setting switch 7. It is to be noted that the relation data between the venous age and the gradient of the rate of change in impedance to the elapsed time has been determined based on the relations between the ages and the rates of change in impedance to the elapsed time for a large number of subjects. Further, the relation data between the venous age and the venous sclerosis level has been determined based on the relation between the ages and the number of patients who have developed the venous sclerosis.

The arithmetic operation and control section 14 comprises a impedance transition gradient calculating unit 15 and a venous distensibility evaluation index determining unit 16, and executes controls and arithmetic operations for respective components as well-known in the art.

The impedance transition gradient calculating unit 15 calculates the rate of change in impedance "Icr" from the equation (1):

$$Icr = (Is - Iw)/Is \times 100 \quad (1)$$

where "Is" is an impedance determined by the impedance conversion section 12 based on the data obtained by sampling before the pressing operation of the vein in one part of the body regions has started and then converting them, and "Iw" is an impedance determined by the impedance conversion section 12 based on the data obtained by sampling after the pressing operation of the vein in one part of the body regions has started and then converting them.

Subsequently, the impedance transition gradient calculating unit 15 uses the least squares method to calculate the correlational expression of the elapsed time measured by the clock section 11, which will be needed to grasp the transient condition of the expansion or the contraction (recovery) of the vein since the starting of the pressing or the decompressing operation of the vein in the one part of the body regions, to the previously calculated rate of change in impedance for each sampling, thereby to specify the gradient of the rate of change in impedance to the elapsed time.

The venous distensibility evaluation index determining unit 16 specifies the venous age corresponding to the gradient of the rate of change in impedance to the elapsed time, which has been calculated in the impedance transition gradient calculating unit 15, based on the relation data between the venous age and the gradient of the rate of change in impedance to the elapsed time, which has been previously stored in the storage section 13, and further specifies the venous sclerosis level corresponding to the previously calculated venous age based on the relation data between the venous age and the venous sclerosis level, which has been previously stored in the storage section 13.

Figure 2:
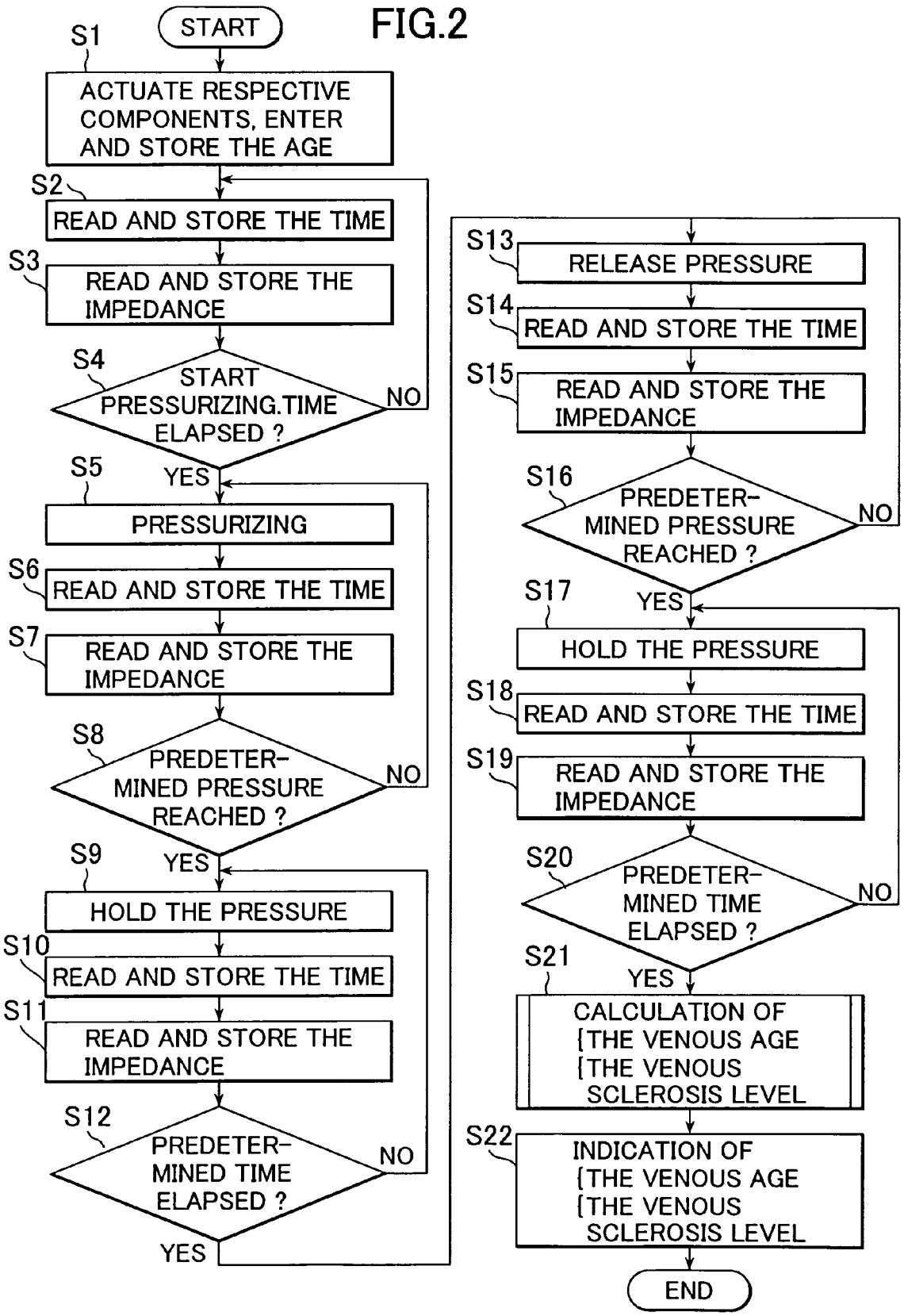
FIG. 2 is a main flow chart showing an application and an operational procedure of a venous distensibility evaluation index measuring apparatus according to the present invention.
Figure 3:
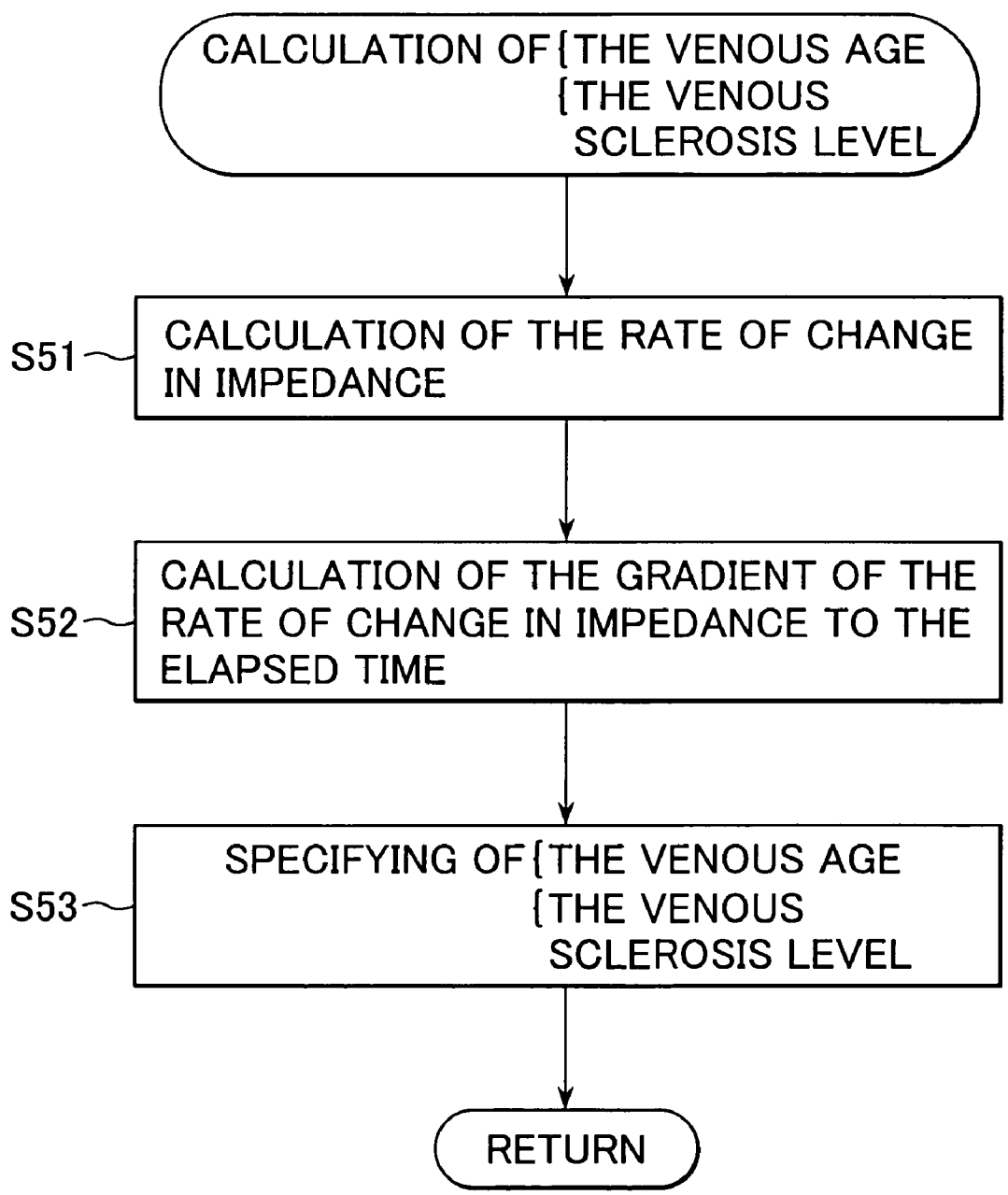
FIG. 3 is a sub-routine flowchart for executing a determining process of an evaluation index of the venous distensibility.

An application and an operational procedure of a venous distensibility evaluation index measuring apparatus according to the present invention will now be described with reference to the main flow chart illustrated in FIG. 2 and the sub routine flow chart illustrated in FIG. 3 for determining and processing the evaluation index of the venous distensibility.

First of all, the venous occluding section (manchette) 3 is wrapped around the upper arm, the conducting electrode 5a and the measuring electrode 5b are affixed to the forearm proximal to the wrist, while another conducting electrode 5a and another measuring electrode 5b are affixed to the forearm proximal to the elbow so as to place the measuring electrodes 5b, 5b to be interposed between the conducting electrodes 5a, 5a, and then the power switch 6 is shifted to ON. By this way, the power supply 9 starts to supply the electric power to respective components of the electric system to bring the respective sections of the apparatus into the activated state. Subsequently, the age (e.g., 34 years) may be entered by using the setting switch 7. By this way, the storage section 13 stores this entered age (Step S1).

Subsequently, the clock section 11 starts to measure the time, the arithmetic operation and control section 14 executes the sampling of said time, and the storage section 13 stores this sampled time (Step S2).

Subsequently, the impedance conversion section 12 generates and applies a current at the frequency of 4 kHz between the conducting electrodes 5a, 5a and converts a voltage detected between the measuring electrodes 5b, 5b in combination with the applied current into an impedance in the forearm, the arithmetic/control section 14 executes a sampling of the impedance in the forearm (i.e., the impedance specified in the condition of the vein with no pressure applied thereto), and the storage section 13 stores said impedance in the forearm obtained by said sampling (the impedance specified in the condition of the vein with no pressure applied thereto) (Step S3).

Subsequently, the arithmetic operation and control section 14 determines whether or not a predetermined time has elapsed since the clock section 11 has started the measuring of the time (Step S4). Herein, the predetermined time is defined by a time period required to ensure the condition of the vein under a rest position of a subject, which is 10 seconds in the present invention. If the predetermined time has not elapsed (NO in Step S4), the process returns back to Step S2 to repeat the same processing. On the other hand, if the predetermined time has elapsed (YES in Step S4), the pressurizing apparatus of the pressure adjusting section 10 generates a pressure to be applied, which in turn is received by the venous occluding section (the manchette) 3 so as to start a squeezing operation of the upper arm (Step S5).

Subsequently, the arithmetic operation and control section 14 executes the sampling of the time under being measured by the clock section 11, and the storage section 13 stores thus sampled time (Step S6).

Subsequently, the arithmetic operation and control section 14 executes the sampling of the impedance in the forearm under being converted by the impedance conversion section 12 (the impedance specified in the condition of the vein with an increasing pressure applied thereto), and the storage section 13 stores thus sampled impedance in the forearm (the impedance specified in the condition of the vein with the increasing pressure applied thereto) (Step S7).

Subsequently, the pressure sensor of the pressure adjusting section 10 detects the pressure used by the venous occluding section (the manchette) 3 to squeeze the upper arm, and the arithmetic operation and control section 14 determined whether or not the pressure of 50 mmHg has been reached (Step S8). If the pressure of 50 mmHg has not been reached (NO in Step S8), the process returns to Step S5 to repeat the same processing. On the other hand, if the pressure of 50 mmHg has been reached (YES in Step S8), the pressure adjusting section 10 keeps on maintaining the pressure of 50 mmHg through the pressurizing operation by the pressurizing apparatus and the control of exhausting in the exhaust valve (Step S9).

Subsequently, the arithmetic operation and control section 14 executes the sampling of the time under being measured by the clock section 11, and the storage section 13 stores thus sampled time (Step S10).

Subsequently, the arithmetic operation and control section 14 executes the sampling of the impedance in the forearm under being converted by the impedance converting section 12 (the impedance specified in the condition of the vein with a constant pressure applied thereto), and the storage section 13 stores thus sampled impedance in the forearm (the impedance specified in the condition of the vein with the constant pressure applied thereto) (Step S11).

Subsequently, the arithmetic operation and control section 14 determines whether or not a predetermined time has elapsed, which has been measured by the clock section 11, since the venous occluding section (the manchette) 3 has started to hold the pressure for squeezing the upper arm (Step S 12). Herein, the predetermined time is defined by a time period required to ensure a stabilized condition of the vein that has been expanded by the occlusion, which is 30 seconds in the present case. If the predetermined time has not elapsed (NO in Step S12), then the process returns back to Step S9 to repeat the same processing. On the other hand, if the predetermined time has elapsed (YES in Step S12), the exhaust valve of the pressure adjusting section 10 is actuated for the exhausting, and in response to this exhausting, the venous occluding section (the manchette) 3 starts to release the squeezing of the upper arm (Step S13).

Subsequently, the arithmetic operation and control section 14 executes the sampling of the time under being measured by the clock section 11, and the storage section 13 stores thus sampled time (Step S14).

Subsequently, the arithmetic operation and control section 14 executes the sampling of the impedance in the forearm under being converted by the impedance conversion section 12 (the impedance specified in the condition of the vein with a decreasing pressure applied thereto), and the storage section 13 stores thus sampled impedance in the forearm (the impedance specified in the condition of the vein with a decreasing pressure applied thereto) (Step S15).

Subsequently, the pressure sensor of the pressure adjusting section 10 detects the pressure used by the venous occluding section (the manchette) 3 to release the squeezing of the upper arm, and the arithmetic operation and control section 14 determines whether or not the pressure of 0 mmHg has been reached (Step S16). If the pressure of 0 mmHg has not been reached (NO in Step S16), then the process returns back to Step S13 to repeat the same processing. On the other hand, if the pressure of 0 mmHg has been reached (YES in Step S16), then the pressure adjusting section 10 keeps the exhausting condition in the exhaust valve to thereby continue to hold the pressure of 0 mmHg (Step S17).

The arithmetic operation and control section 14 executes the sampling of the time under being measured by the clock section 11, and the storage section 13 stores thus sampled time (Step S18).

Subsequently, the arithmetic operation and control section 14 executes the sampling of the impedance in the forearm under being converted by the impedance conversion section 12 (the impedance specified in the condition of the vein with a constant decreased pressure applied thereto), and the storage section 13 stores thus sampled impedance in the forearm (the impedance specified in the condition of the vein with the constant decreased pressure applied thereto) (Step S19).

Subsequently, the arithmetic operation and control section 14 determines whether or not a predetermined time has elapsed, which has been measured by the clock section 11, since the venous occluding section (the manchette) 3 has started to keep the releasing operation of the squeezing of the upper arm (Step S20). Herein, the predetermined time is defined by a time period required to ensure the stabilized condition of the vein that has been contracted (recovered) by the releasing of the occlusion, which is 30 seconds in the present invention. If the predetermined time has not elapsed (NO in Step S20), the process returns back to Step S17 to repeat the same processing. On the other hand, if the predetermined time has elapsed (YES in Step S20), the arithmetic operation and control section 14 determines the venous age and the venous sclerosis level as the evaluation index of the venous distensibility (Step S21), the display section 8 indicates a determination result of the venous age and the venous sclerosis level as well as an advice on a possibility of any vascular diseases, and so on (Step S 22), and the process comes to the end.

The process in Step S21 for determining the evaluation index of the venous distensibility (the venous age, the venous sclerosis level) will now be described in more specific.

After the YES in Step S20, the impedance transition gradient calculating unit 15 firstly calculates the rate of change in impedance (Step S51). To describe this in more specific, the first impedance in the forearm stored in the storage section 13 in Step S13 (the impedance specified in the condition of the vein with no pressure applied thereto) is substituted for Is of the equation (1) described above, and the impedance in the forearm stored in the storage section 13 after the venous occluding section 13 (the manchette) has started to squeeze the upper arm in Step S5 (the impedance specified in the condition of the vein with the increasing pressure, with the constant pressure, with the decreasing pressure, and with no pressure applied thereto respectively) is substituted for Iw of the equation (1) described above so as to calculate the rate of change in impedance, Icr.

Subsequently, the impedance transition gradient calculating unit 15 executes an arithmetic operation to determine the gradient (absolute value) of the rate of change in impedance to the elapsed time (Step S52). To describe in more specific, for example, if the relation between the rate of change in impedance and the elapsed time, which has been described above, is represented in the graph of FIG. 4, then the least squares method is used to calculate the correlational expression $Y=-\alpha \times \log X + \beta$ to thereby specify the gradient (absolute value) "$\alpha$" (numeric value) of the rate of change in impedance with respect to the elapsed time specified for the conditions with the increasing pressure and the constant pressure applied to the vein, where the "Y" denotes the rate of change in impedance previously calculated in Step S 51 and the "X" denotes the elapsed time stored in the storage section 13 as defined from the time when the venous occluding section (the manchette) 3 has started the squeezing of the upper arm in Step S5 until the clock section 11 has counted the predetermined elapsed time in the YES of Step 12.

Subsequently, the venous distensibility evaluation index determining unit 16 specifies the venous age and the venous sclerosis level (Step S53). To describe this in more specific, first of all, the gradient (absolute value) "$\alpha$" (numeric value) of the rate of change in impedance to the elapsed time for the conditions with the increasing pressure and the constant pressure applied to the vein, each of which has been specified by the impedance transition gradient calculating unit 15, is substituted for the variable term "Sit" of such a relation data (correlational expression $Va=-\gamma \times Sit + \delta$) between the venous age and the gradient (absolute value) of the rate of change in impedance to the elapsed time as represented in the graph of FIG. 5, which has been stored previously in the storage section 13, thereby calculating the venous age expressed by the numeric value. Subsequently, the venous sclerosis level corresponding to the venous age determined as described above is specified from such a relation data between the venous age and the venous sclerosis level as shown in the table of FIG. 6, which has been previously stored in the storage section 13. For example, if the venous age that has been determined as described above by the numeric value is the age of 26, the venous sclerosis level is specified to be level 0 that corresponds to the age of 26. Further, this operation also determines the possibility in the expression of "extremely low" for the vascular disease that corresponds to the venous age of 26, and then the process exits the present sub-routine.

As described above, in the venous distensibility evaluation index measuring apparatus according to the present invention, the storage section 13 stores in advance the relation data between the venous age and the gradient of the rate of change in impedance to the elapsed time as well as the relation data between the venous age and the venous sclerosis level, the venous occluding section 3 brings the vein in the upper arm into the condition where it is pressed at the constant pressure of 50 mmHg, the pressure adjusting section 10 adjusts the pressure to be increased or decreased in order to hold the vein under the condition where it is pressed at the constant pressure of 50 mmHg, the clock section 11 measures the elapsed time from the starting of the pressed condition of the vein, the electrode section generates and applies the current at 4 kHz to the forearm, and also detects the voltage at that time, the impedance conversion section 12 converts the detected voltage in combination with the applied current into the impedance, the impedance transition gradient calculating unit 15 determines the gradient of the rate of change in impedance to the elapsed time, the venous distensibility evaluation index determining unit 16 determines the venous age corresponding to the gradient of the rate of change in impedance to the elapsed time, and further determines the venous sclerosis level corresponding to the determined venous age, and the display section 8 indicates the venous age and the venous sclerosis level. Owing to the configuration described above, the venous age and the venous sclerosis level can be obtained in a simple and convenient manner without any intervenient persons.

It is to be noted that in the above-described embodiment, the pressure of 50 mmHg has been employed in the venous occluding section 3 in order to hold the vein of the upper arm under the constant pressure, and this pressure of 50 mmHg is the one to optimally bring the vein in the upper arm exclusively into the pressed condition. However, any pressure in a range of 30 mmHg to 90 mmHg may be employed to hold the vein in the upper arm under the constant pressure.

Further, the current to be applied to the forearm so as to flow therethrough by the electrode section has been at the frequency of 4 kHz, and this frequency of 4 kHz is the one to achieve the optimal condition for the current to flow through the vein in the forearm. However, the current at the frequency in a range of 1 kHz to 500 kHz may be employed to flow through the forearm.

Figure 4:
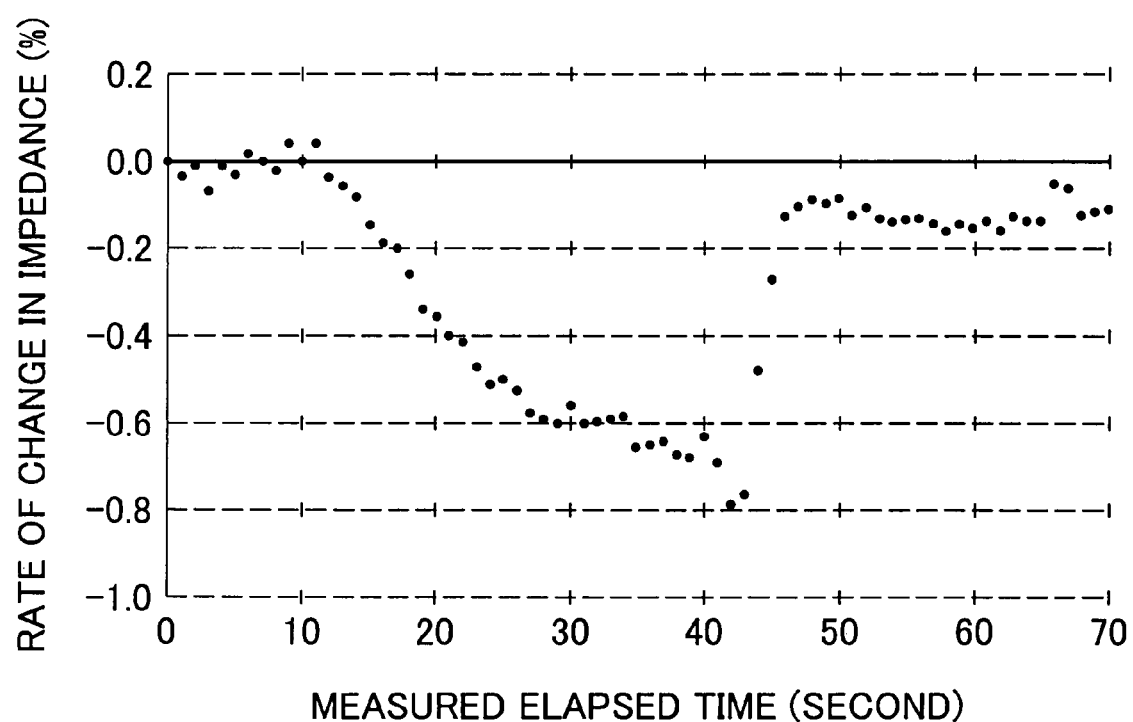
FIG. 4 is a graphical representation showing an exemplary measured relationship between a rate of change in impedance to an elapsed time.

Yet further, although in the impedance transition gradient calculating unit 15, the gradient has been specified by using the correlational expression for calculating the rate of change in impedance for the period of 30 seconds (the measured elapsed time from 10th second to 40th second as shown in FIG. 4) defined as from the time when the venous occluding section (the manchette) 3 has started to squeeze the upper arm (Step S5) until the predetermined time has elapsed (YES in Step S12), alternatively the gradient may be determined by using the correlational expression for calculating the rate of change in impedance for a part of the time zone within said 30 seconds. For example, the gradient (absolute value) "$\epsilon$" (numeric value) may be specified, by using the least square method, from the correlational expression ($Y=-\epsilon \times X+\zeta$, in FIG. 4) for calculating the rate of change in impedance for 17 seconds (the elapsed time defined in the period from 10th second to 27th second as shown in FIG. 4) measured as the period of 17 seconds from the time when the venous occluding section (the manchette) 3 has started to squeeze the upper arm (Step S5).

Alternatively, the impedance transition gradient calculating unit 15 may calculate the gradient by using the correlational expression for calculating the rate of change in impedance to the elapsed time since the venous occluding section (the manchette) 3 has started to release the squeezing of the upper arm (Step S13). For example, the gradient maybe calculated by using the correlational expression for calculating the rate of change in impedance to the time period of 3 seconds (the elapsed time defined from 43rd second to 46th second, as shown in FIG. 4) measured as the time period from 3rd second to 6th second after the manchette has started to release the squeezing of the upper arm (Step S13).

Further, although the storage section 13 has stored in advance the relation data between the gradient of the rate of change in impedance to the elapsed time and the venous age as well as the relation date between the venous age and the venous sclerosis level, and the venous distensibility evaluation index determining unit 16 has determined the venous age and the venous sclerosis level in this sequence from the gradient of the rate of change in impedance to the elapsed time, which has been determined by the impedance transition gradient calculating unit 15, alternatively the venous sclerosis level and the venous age may be determined in this sequence. In this case, if the storage section 13 stores the relation data between the gradient of the rate of change in impedance to the elapsed time and the venous sclerosis level as well as the relation data between the venous sclerosis level and the venous age, then the venous distensibility evaluation index determining unit 16 can determine similarly the venous sclerosis level and the venous age in this sequence.

Further, although the venous age and the venous sclerosis level have been determined as the venous distensibility evaluation indices, either one of those may be exclusively determined. Yet further, the evaluation index for the venous distensibility may not be limited to the venous age or the venous sclerosis level. As for the index for evaluating the venous distensibility, any indices by which the subject can get some awareness may be used, especially the one that can lead to the prediction in association with diseases may be more preferably used.

Further, although the evaluation index of the venous distensibility of the arm has been measured, alternatively the measurement in the leg or other body regions may be similarly applicable. For example, the venous occluding section 3 may be wrapped to squeeze around the thigh, and the electrode 5 may be disposed on the lower thigh thus to provide the measurement.

As described above, according to the venous distensibility evaluation index measuring apparatus of the present invention, under the condition where the venous occluding section brings the vein in one part of the body regions into the pressed state or from the pressed state to the decompressed state, the electrode section detects the volumetric change due to the expansion or the contraction (recovery) of the vein in a location more distant from the heart with respect to that of the venous occluding section yet in the same circulation path as said vein of the one part of the body regions, the impedance conversion section converts the detected data into the impedance, the impedance transition gradient calculating unit determines the gradient of the rate of change in impedance to the elapsed time, the venous distensibility evaluation index determining unit specifies the evaluation index of the volumetric change due to the expansion or the contraction (recovery) of the vein, namely the evaluation index of the venous distensibility, and finally the display section may indicate the evaluation index of the venous distensibility. Therefore, the evaluation index of the venous distensibility can be determined and informed of in a simple and convenient way without disturbing any intervenient persons.

Further, the vein in one part of the body regions can be occluded exclusively by providing the pressed condition where an applied pressure is controlled to be constant within a range from 30 mmHg to 90 mmHg, wherein the vein in one part of the body regions can be exclusively and reliably occluded by providing the pressed condition where the applied pressure is controlled to be at a constant pressure of 50 mmHg among others.

Yet further, the volumetric change due to the expansion or the contraction (recovery) of the vein can be reliably detected by providing a predetermined frequency in a range from 1 kHz to 500 kHz, wherein the volumetric change due to the expansion or the contraction (recovery) of the vein can be detected more reliably by providing the predetermined frequency of 4 kHz among others.

Still further, the evaluation of useful information including the prediction of the possible vascular disease can be provided since the venous distensibility evaluation index is represented by the venous age and the venous sclerosis level, each of which has a correlation with the vascular disease. Especially since both of the venous age and the venous sclerosis level are determined by the venous distensibility evaluation index determining unit, the evaluation relating to the prediction of the vascular disease can be provided from broadly different points of view.

What is claimed is:

1. A venous distensibility evaluation index measuring apparatus comprising:
   a venous occluding section;
   a pressure adjusting section;
   a clock section;
   an electrode section;
   an impedance conversion section;
   an impedance transition gradient calculating unit;
   a storage section;
   a venous distensibility evaluation index determining unit; and
   a display section;
   wherein said venous occluding section causes a vein in one part of body regions to be in a pressed condition;

said pressure adjusting section adjusts a pressure used to cause the vein in the one part of the body regions to be in the pressed condition by increasing or decreasing the pressure, which is to be supplied to said venous occluding section;

said clock section measures an elapsed time since said venous occluding section has started the pressing operation of said vein in the one part of the body regions;

said electrode section supplies a current at a predetermined frequency to a vein in a location more distant from the heart with respect to that of said venous occluding section yet in the same circulation path as said vein of the one part of the body regions, while detecting a voltage, when said clock section measures said elapsed time;

said impedance conversion section generates said current at the predetermined frequency to be supplied by said electrode section, while converting said voltage detected by said electrode section in combination with the supplied current into an impedance;

said impedance transition gradient calculating unit arithmetically calculates a gradient of a rate of change in impedance to the elapsed time based on said impedance converted in said impedance conversion section and said elapsed time measured by said clock section;

said storage section stores previously data indicative of a relation between the gradient of the rate of change in impedance to the elapsed time and a first venous distensibility evaluation index;

said venous distensibility evaluation index determining unit specifies said first venous distensibility evaluation index corresponding to said gradient of the rate of change in impedance to the elapsed time calculated by said impedance transition gradient calculating unit from said relation data stored previously in said storage section; and said display section indicates said first venous distensibility evaluation index specified by said venous distensibility evaluation index determining unit.

2. A venous distensibility evaluation index measuring apparatus in accordance with claim 1, in which said pressed condition represents a condition pressed at a constant pressure in a range from 30 mmHg to 90 mmHg.

3. A venous distensibility evaluation index measuring apparatus in accordance with claim 1, in which said pressed condition represents a condition pressed at a constant pressure of 50 mmHg.

4. A venous distensibility evaluation index measuring apparatus in accordance with claim 1, in which said predetermined frequency is in a range from 1 kHz to 500 kHz.

5. A venous distensibility evaluation index measuring apparatus in accordance with claim 2, in which said predetermined frequency is in a range from 1 kHz to 500 kHz.

6. A venous distensibility evaluation index measuring apparatus in accordance with claim 3, in which said predetermined frequency is in a range from 1 kHz to 500 kHz.

7. A venous distensibility evaluation index measuring apparatus in accordance with claim 1, in which said predetermined frequency is 4 kHz.

8. A venous distensibility evaluation index measuring apparatus in accordance with claim 2, in which said predetermined frequency is 4 kHz.

9. A venous distensibility evaluation index measuring apparatus in accordance with claim 3, in which said predetermined frequency is 4 kHz.

10. A venous distensibility evaluation index measuring apparatus in accordance with either one of claims 1 through 9, in which said first venous distensibility evaluation index is either one of a venous age or a venous sclerosis level.

11. A venous distensibility evaluation index measuring apparatus in accordance with claim 10, in which said storage section stores a correlational expression $Va=-\gamma \times Sit+\delta$ as the relation data between the gradient of the rate of change in impedance to the elapsed time and the venous age, where the Sit denotes the gradient of the rate of change in impedance to the elapsed time, the Va denotes the venous age, and the $\gamma$ and the $\delta$ denote coefficients, respectively, and said venous distensibility evaluation index determining unit calculates said venous age corresponding to said gradient of the rate of change in impedance to the elapsed time calculated by said impedance transition gradient calculating unit based on said correlational expression stored previously in said storage section.

12. A venous distensibility evaluation index measuring apparatus in accordance with either one of claims 1 through 9, in which said storage section further stores previously data indicative of a relation between said first venous distensibility evaluation index and a second venous distensibility evaluation index, and said venous distensibility evaluation index determining unit specifies said second venous distensibility evaluation index corresponding to said first venous distensibility evaluation index specified previously, from said relation data stored further previously in said storage section.

13. A venous distensibility evaluation index measuring apparatus in accordance with claim 12, in which said first venous distensibility evaluation index represents either one of the venous age or the venous sclerosis level, and said second venous distensibility evaluation index represents the venous sclerosis level if said first venous distensibility evaluation index is the venous age, and said second venous distensibility evaluation index represents the venous age if said first venous distensibility evaluation index is the venous sclerosis level.

14. A venous distensibility evaluation index measuring apparatus in accordance with claim 13, in which said storage section stores a correlational expression $Va=-\gamma \times Sit+\delta$ as the relation data between the gradient of the rate of change in impedance to the elapsed time and the venous age, where the Sit denotes the gradient of the rate of change in impedance to the elapsed time, the Va denotes the venous age, and the $\gamma$ and the $\delta$ denote coefficients, respectively, and said storage section further stores corresponding data as the relation data between the venous age and the venous sclerosis level, which is indicated by the level 0 of the venous sclerosis level for the venous age no older than 39, the level 1 for the venous age in a range of 40 to 49, the level 2 for the venous age in a range of 50 to 59 and the level 3 for the venous age no younger than 65, and said venous distensibility evaluation index determining unit calculates said venous age corresponding to said gradient of the rate of change in impedance to the elapsed time calculated by said impedance transition gradient calculating unit based on said correlational expression stored previously in said storage section, and said venous distensibility evaluation index determining unit further specifies said venous sclerosis level corresponding to said venous age calculated previously, from said corresponding data stored further previously in said storage section.

15. A venous distensibility evaluation index measuring apparatus comprising:

a venous occluding section;

a pressure adjusting section;
a clock section;
an electrode section;
an impedance conversion section;
an impedance transition gradient calculating unit;
a storage section;
a venous distensibility evaluation index determining unit; and
a display section;
wherein said venous occluding section causes a vein in one part of body regions to be shifted from a pressed condition into a decompressed condition;
said pressure adjusting section adjusts a pressure used to cause the vein in the one part of the body regions to be shifted from the pressed condition into the decompressed condition by increasing or decreasing the pressure, which is to be supplied to said venous occluding section;
said clock section measures an elapsed time since said venous occluding section has started the decompressing operation of said vein in the one part of the body regions;
said electrode section supplies a current at a predetermined frequency to a vein in a location more distant from the heart with respect to that of said venous occluding section yet in the same circulation path as said vein of the one part of the body regions, while detecting a voltage, when said clock section measures said elapsed time;
said impedance conversion section generates said current at the predetermined frequency to be supplied by said electrode section, while converting said voltage detected by said electrode section in combination with the supplied current into an impedance;
said impedance transition gradient calculating unit arithmetically calculates a gradient of a rate of change in impedance to the elapsed time based on said impedance converted in said impedance conversion section and said elapsed time measured by said clock section;
said storage section stores previously data indicative of a relation between the gradient of the rate of change in impedance to the elapsed time and a first venous distensibility evaluation index;
said venous distensibility evaluation index determining unit specifies said first venous distensibility evaluation index corresponding to said gradient of the rate of change in impedance to the elapsed time calculated by said impedance transition gradient calculating unit from said relation data stored previously in said storage section; and
said display section indicates said first venous distensibility evaluation index specified by said venous distensibility evaluation index determining unit.

16. A venous distensibility evaluation index measuring apparatus in accordance with claim 15, in which said pressed condition represents a condition pressed at a constant pressure in a range from 30 mmHg to 90 mmHg.

17. A venous distensibility evaluation index measuring apparatus in accordance with claim 15, in which said pressed condition represents a condition pressed at a constant pressure of 50 mmHg.

18. A venous distensibility evaluation index measuring apparatus in accordance with claim 15, in which said predetermined frequency is in a range from 1 kHz to 500 kHz.

19. A venous distensibility evaluation index measuring apparatus in accordance with claim 16, in which said predetermined frequency is in a range from 1 kHz to 500 kHz.

20. A venous distensibility evaluation index measuring apparatus in accordance with claim 17, in which said predetermined frequency is in a range from 1 kHz to 500 kHz.

21. A venous distensibility evaluation index measuring apparatus in accordance with claim 15, in which said predetermined frequency is 4 kHz.

22. A venous distensibility evaluation index measuring apparatus in accordance with claim 16, in which said predetermined frequency is 4 kHz.

23. A venous distensibility evaluation index measuring apparatus in accordance with either one of claim 17, in which said predetermined frequency is 4 kHz.

24. A venous distensibility evaluation index measuring apparatus in accordance with either one of claims 15 through 23, in which said first venous distensibility evaluation index is either one of a venous age or a venous sclerosis level.

25. A venous distensibility evaluation index measuring apparatus in accordance with either one of claims 15 through 23, in which said storage section further stores previously data indicative of a relation between said first venous distensibility evaluation index and a second venous distensibility evaluation index, and said venous distensibility evaluation index determining unit specifies said second venous distensibility evaluation index corresponding to said first venous distensibility evaluation index specified previously, from said relation data stored further previously in said storage section.

26. A venous distensibility evaluation index measuring apparatus in accordance with claim 25, in which said first venous distensibility evaluation index represents either one of the venous age or the venous sclerosis level, and said second venous distensibility evaluation index represents the venous sclerosis level if said first venous distensibility evaluation index is the venous age, and said second venous distensibility evaluation index represents the venous age if said first venous distensibility evaluation index is the venous sclerosis level.

* * * * *